(12) United States Patent
Hahn et al.

(10) Patent No.: US 10,827,748 B2
(45) Date of Patent: Nov. 10, 2020

(54) CARBONATES OF ALCOHOL ALKOXYLATES AS ADJUVANTS FOR CROP PROTECTION

(71) Applicant: BASF SE, Ludwigshafen (DE)

(72) Inventors: Bjorn Thomas Hahn, Dusseldorf (DE); Rainer Berghaus, Speyer (DE); Martin Semar, Gleiszellen-Gleishorbach (DE); Hans-Christian Raths, Monheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/285,270

(22) Filed: Feb. 26, 2019

(65) Prior Publication Data
US 2019/0183119 A1    Jun. 20, 2019

Related U.S. Application Data

(62) Division of application No. 15/125,042, filed as application No. PCT/EP2015/052449 on Feb. 5, 2015, now Pat. No. 10,238,106.

(30) Foreign Application Priority Data

Mar. 12, 2014 (EP) ..................................... 14159195
Aug. 12, 2014 (EP) ..................................... 14180690

(51) Int. Cl.
| A01N 25/30 | (2006.01) |
| C07C 69/96 | (2006.01) |
| C08G 65/26 | (2006.01) |
| A01N 31/02 | (2006.01) |
| A01N 43/56 | (2006.01) |
| A01N 43/653 | (2006.01) |

(52) U.S. Cl.
CPC .............. *A01N 31/02* (2013.01); *A01N 25/30* (2013.01); *A01N 43/56* (2013.01); *A01N 43/653* (2013.01); *C07C 69/96* (2013.01); *C08G 65/2603* (2013.01)

(58) Field of Classification Search
CPC ........ A01N 25/30; C07C 69/96; C08G 65/26; C08G 65/2603
See application file for complete search history.

(56) References Cited

U.S. PATENT DOCUMENTS

| 5,492,631 A | 2/1996 | Koester et al. |
| 6,147,246 A | 11/2000 | Weerasooriya et al. |
| 6,156,705 A ‡ | 12/2000 | Mueninghoff ......... A01N 25/30 504/36 |
| 2008/0317694 A1 ‡ | 12/2008 | Bruening ................ A61K 8/26 424/66 |
| 2010/0298448 A1 | 11/2010 | Krause et al. |
| 2012/0115730 A1 | 5/2012 | Mainx et al. |
| 2013/0130912 A1 | 5/2013 | Tannir et al. |

FOREIGN PATENT DOCUMENTS

| CN | 103153047 A | | 6/2013 |
| DE | 4404200 | ‡ | 8/1995 |
| WO | WO-2013/189745 | ‡ | 12/2013 |
| WO | WO-2014/095932 | ‡ | 6/2014 |
| WO | WO-2014/095994 | ‡ | 6/2014 |
| WO | WO-2015/003908 | ‡ | 1/2015 |
| WO | WO-2015/059063 | ‡ | 4/2015 |
| WO | WO-2015/071139 | ‡ | 5/2015 |
| WO | WO-2015/113860 | ‡ | 8/2015 |
| WO | WO-2015/121102 | ‡ | 8/2015 |
| WO | WO-2015/135701 | ‡ | 9/2015 |
| WO | WO-2015/140102 | ‡ | 9/2015 |
| WO | WO-2015/165760 | ‡ | 11/2015 |
| WO | WO-2015/169711 | ‡ | 11/2015 |
| WO | WO-2015/197392 | ‡ | 12/2015 |
| WO | WO-2015/197393 | ‡ | 12/2015 |
| WO | 16041693 A1 | | 3/2016 |

OTHER PUBLICATIONS

Grayson et al., "Effects of Adjuvants on the Performance of the New Cereal Fungicide, Metconazole. I Glasshouse Trials," Pesticide Science, 1995, vol. 45, No. 2, pp. 153-160.‡
International Search Report for PCT/EP2015/052449 dated Mar. 17, 2015.‡

‡ imported from a related application

*Primary Examiner* — John Pak
(74) *Attorney, Agent, or Firm* — Marshall, Gerstein & Borun LLP

(57) ABSTRACT

The present invention relates to an agrochemical composition comprising a pesticide and an alkoxylate of the formula (I) as defined below. The invention further relates to said alkoxylate. The invention further relates to a method of preparing said composition by bringing the alkoxylate and the pesticide into contact. Finally, the invention relates to a method of controlling phytopathogenic fungi and/or undesired plant growth and/or undesired insect or mite attack and/or for regulating the growth of plants, wherein said composition is allowed to act on the respective pests, their environment or the crop plants to be protected from the respective pest, on the soil and/or on undesired plants and/or on the crop plants and/or on their environment; and to seed containing said composition.

14 Claims, No Drawings

CARBONATES OF ALCOHOL ALKOXYLATES AS ADJUVANTS FOR CROP PROTECTION

CROSS-REFERENCE TO PRIOR APPLICATIONS

This application is a divisional of U.S. application Ser. No. 15/125,042, filed Sep. 9, 2016, the entire contents of which is hereby incorporated herein by reference. U.S. patent application Ser. No. 15/125,042 is a National Stage application of International Application No. PCT/EP2015/052449, filed Feb. 5, 2015, the entire contents of which are hereby incorporated herein by reference. U.S. application Ser. No. 15/125,042 also claims priority under 35 U.S.C. § 119 to European Application No. 14159195.8, filed Mar. 12, 2014, and European Application No. 14180690.1, filed Aug. 12, 2014, the entire contents of both of which are hereby incorporated herein by reference.

DESCRIPTION

The present invention relates to an agrochemical composition comprising a pesticide and an alkoxylate of the formula (I) as defined below. The invention further relates to said alkoxylate. The invention further relates to a method of preparing said composition by bringing the alkoxylate and the pesticide into contact. Finally, the invention relates to a method of controlling phytopathogenic fungi and/or undesired plant growth and/or undesired insect or mite attack and/or for regulating the growth of plants, wherein said composition is allowed to act on the respective pests, their environment or the crop plants to be protected from the respective pest, on the soil and/or on undesired plants and/or on the crop plants and/or on their environment; and to seed containing said composition. The preferred embodiments of the invention mentioned herein below have to be understood as being preferred either independently from each other or in combination with one another.

Adjuvants are important agroformulation auxiliaries and assist in improving the stability of the formulation and the efficacy of the pesticide. It is an ongoing challenge to identify new adjuvants with improved properties.

Object of the present invention was to overcome the problems of the state of the art. The object was solved by a composition comprising a pesticide and an alkoxylate of the formula (I)

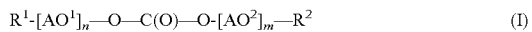

$$R^1\text{-}[AO^1]_n\text{---}O\text{---}C(O)\text{---}O\text{-}[AO^2]_m\text{---}R^2 \quad (I)$$

where
$R^1$ and $R^2$ are independently a $C_6$-$C_{32}$ hydrocarbon group,
$AO^1$ and $AO^2$ are independently a $C_2$-$C_6$ alkyleneoxy group, and
n and m are independently a value from 2 to 100.

In another form the object was solved by the alkoxylate of the formula (I).

The term agrochemical composition refers usually to a composition which is suitable for a industrial application in controlling phytopathogenic fungi and/or undesired plant growth and/or undesired insect or mite attack and/or for regulating the growth of plants, wherein the composition is allowed to act on the respective pests, their environment or the crop plants to be protected from the respective pest, on the soil and/or on undesired plants and/or on the crop plants and/or on their environment. Industrial application of agrochemical compositions are usually subject to various specific legal restrictions and specific registration processes. An expert is well aware that other composition, such as deodorizing or pharmaceutical preparations, as well as cosmetics, are usually not suitable for an industrial application in controlling phytopathogenic fungi and/or undesired plant growth and/or undesired insect or mite attack and/or for regulating the growth of plants, wherein the composition is allowed to act on the respective pests, their environment or the crop plants to be protected from the respective pest, on the soil and/or on undesired plants and/or on the crop plants and/or on their environment.

$R^1$ and $R^2$ are independently usually a monovalent $C_6$-$C_{32}$ aliphatic hydrocarbon group, preferably a linear or branched, saturated or unsaturated $C_8$-$C_{20}$ alkyl. More preferably, $R^1$ and $R^2$ are independently a linear or branched, saturated $C_{10}$-$C_{18}$ alkyl. Mixtures of different hydrocarbon groups are also possible, such as mixtures of different chain lengths, and/or of saturated and unsaturated hydrocarbons. In one form $R^1$ and $R^2$ are identical. In another form $R^1$ and $R^2$ are different.

Typical examples for $R^1$ or $R^2$ are linear or branched decyl, undecyl, dodecyl, tridecyl, hexa-decyl, heptadecyl and octadecyl, or mixture of the aforementioned residues. In another form examples for $R^1$ or $R^2$ are selected from branched $C_{13}$ alkyl. In another form examples for $R^1$ or $R^2$ are selected from linear $C_{12}$-$C_{18}$ alkyl. In another form examples for $R^1$ or $R^2$ are selected from branched $C_{10}$ alkyl, such as 2-propylheptyl. In another form $R^1$ and $R^2$ are independently a branched $C_{10}$ alkyl. In an especially preferred form, $R^1$ and $R^2$ are 2-propylheptyl.

$AO^1$ and $AO^2$ are independently usually a saturated or unsaturated, linear or branched $C_2$-$C_6$ alkyleneoxy group. Mixtures of different $C_2$-$C_6$ alkyleneoxy group are also possible (e.g. $AO^1$ and $AO^2$ are each independently a mixture of ethyleneoxy and a $C_3$-$C_6$ alkyleneoxy group, wherein a mixture of ethyleneoxy and propyleneoxy is preferred). Examples for $AO^1$ or $AO^2$ are independently ethyleneoxy, propyleneoxy, butyleneoxy, or mixtures thereof. $AO^1$ or $AO^2$ are more preferably independently ethylenoxy, or a mixture of ethyleneoxy and propyleneoxy. In particular, $AO^1$ and $AO^2$ are ethyleneoxy.

The indices n and m are independently usually any value from 2 to 100, preferably from 2.2 to 50, more preferably from 2.5 to 20, and in particular from 3 to 13.

The ratio of n to m is usually from 10/1 to 1/10, preferably from 3/1 to 1/3, more preferably from 2/1 to 1/2, and in particular from 1.5/1 to 1/1.5.

In another form the alkoxylate is of the formula (I) where $R^1$ and $R^2$ are independently a linear or branched, saturated or unsaturated $C_8$-$C_{20}$ alkyl, $AO^1$ and $AO^2$ are independently ethyleneoxy, or ethyleneoxy and propyleneoxy, and n and m are independently from 2 to 50.

In another form the alkoxylate is of the formula (I) where $R^1$ and $R^2$ are independently a linear or branched, saturated or unsaturated $C_8$-$C_{20}$ alkyl, $AO^1$ and $AO^2$ are ethyleneoxy, and n and m are independently from 2.5 to 20.

In another form the alkoxylate is of the formula (I) where $R^1$ and $R^2$ are 2-propylheptyl, $AO^1$ and $AO^2$ are independently ethyleneoxy, or ethyleneoxy and propyleneoxy, and n and m are independently from 2 to 30.

In another form the alkoxylate is of the formula (I) where $R^1$ and $R^2$ are independently linear $C_{12}$-$C_{18}$ alkyl, $AO^1$ and $AO^2$ are independently ethyleneoxy, or ethyleneoxy and propyleneoxy, and n and m are independently from 2 to 30.

In another form the alkoxylate is of the formula (I) where $R^1$ and $R^2$ are independently branched $C_{13}$ alkyl, $AO^1$ and $AO^2$ are independently ethyleneoxy, or ethyleneoxy and propyleneoxy, and n and m are independently from 2 to 30.

In a form the alkoxylate is of formula (I), where $AO^1$ and $AO^2$ are ethyleneoxy. This form corresponds to the alkoxylate of formula (II)

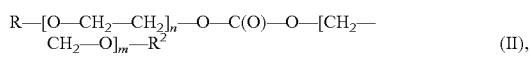

$$R-[O-CH_2-CH_2]_n-O-C(O)-O-[CH_2-CH_2-O]_m-R^2 \quad (II),$$

where $R^1$, $R^2$, n and m have the meanings and preferred forms as defined above.

The alkoxylates of the formula (I) and (II) may be prepared by the reaction of a dialkyl carbonate (e.g. diethyl carbonate or dimethyl carbonate, wherein the latter is preferred) with an alkyl alkoxylate. Suitable alkyl alkoxylates are those of the formula (III)

$$R^1-[AO^1]_n-O-H \quad (III)$$

where $R^1$, $AO^1$ and n have the meaning as described above. The reaction may be catalyzed by alkaline catalysts, such as sodium methylate. Usually, the reaction temperature is between 15 and 250° C. Various means, such as vacuum, may be used to remove byproducts (e.g. ethanol from diethyl carbonate). The reaction product may be further purified to obtain the alkoxylate of the formula (I) or (II). In a preferred form the reaction product containing the alkoxylate of the formula (I) or (II) may be used as technical quality without further purification. The technical quality of the reaction product may comprise up to 40 wt %, preferably up to 25 wt % and more preferably up to 15 wt % of starting materials or byproducts.

The composition may contain at least 0.1 wt %, preferably at least 1 wt % of the alkoxylate of formula (I). The composition according to the invention may be present as an agrochemical composition type and comprises from 1 to 80% by weight of the alkoxylate of formula (I), preferably from 2 to 50% by weight and in particular from 5 to 30% by weight.

The term pesticide refers to at least one active substance selected from the group of the fungicides, insecticides, nematicides, herbicides, safeners, biopesticides and/or growth regulators. Preferred pesticides are fungicides, insecticides, herbicides and growth regulators. Especially preferred pesticides are fungicides. Mixtures of pesticides of two or more of the abovementioned classes may also be used. The skilled worker is familiar with such pesticides, which can be found, for example, in the Pesticide Manual, 16th Ed. (2013), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothi-adiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

Preferably, the pesticide is soluble in water up to 10 g/l, preferably up to 1 g/l, and in particular up to 0.5 g/l, at 20° C.

The composition according to the invention may also be present in form of an agrochemical formulation comprising the pesticide, the alkoxylate of the formula (I), and optionally an auxiliary. An agrochemical formulation comprises usually a pesticidally effective amount of a pesticide. The term "effective amount" denotes an amount of the composition or of the compounds I, which is sufficient for controlling harmful pests on or around cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific pesticide used.

Suitable, customary types of agrochemical compositions are e.g. solutions, emulsions, suspensions, dusts, powders, pastes, granules, pressings, capsules, and mixtures thereof. Examples for formulation types are suspensions (e.g. SC, OD, FS), emulsifiable concentrates (e.g. EC), dispersible concentrates (DC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further formulation types are defined in the "Catalogue of pesticide formulation types and international coding system", Technical Monograph No. 2, 6th Ed. May 2008, CropLife International.

The agrochemical formulations are often prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, further adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, lime-stone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylate surfactants, N-substituted fatty acid amides, amine oxides, esters, sugar-based surfactants, polymeric surfactants, and mixtures thereof. Examples of alkoxylate surfactants are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide.

Suitable polyelectrolytes are polyacids or polybases. Examples of polyacids are alkali salts of polyacrylic acid or polyacid comb polymers. Examples of polybases are polyvinylamines or polyethyleneamines.

Suitable further adjuvants are compounds, which have a neglectable or even no pesticidal activity themselves, and which improve the biological performance of the pesticide on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for formulation types and their preparation are:
i) Water-soluble concentrates (SL, LS)

10-60 wt % of the pesticide and 5-15 wt % wetting agent (e.g. alcohol alkoxylates) are dissolved in water and/or in a water-soluble solvent (e.g. alcohols) up to 100 wt %. The active substance dissolves upon dilution with water.
ii) Dispersible concentrates (DC)

5-25 wt % of the pesticide and 1-10 wt % dispersant (e.g. polyvinylpyrrolidone) are dissolved in up to 100 wt % organic solvent (e.g. cyclohexanone). Dilution with water gives a dispersion.
iii) Emulsifiable concentrates (EC)

15-70 wt % of the pesticide and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.
iv) Emulsions (EW, EO, ES)

5-40 wt % of the pesticide and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of the pesticide are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of the pesticide are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)

50-80 wt % of the pesticide are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of the pesticide are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

iv) Microemulsion (ME)

5-20 wt % of the pesticide are added to 5-30 wt % organic solvent blend (e.g. fatty acid dimethyl-amide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of the pesticide, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of the pesticide, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable powders (DP, DS)

1-10 wt % of the pesticide are ground finely and mixed intimately with up to 100 wt % solid carrier, e.g. finely divided kaolin.

x) Granules (GR, FG)

0.5-30 wt % of the pesticide is ground finely and associated with up to 100 wt % solid carrier (e.g. silicate). Granulation is achieved by extrusion, spray-drying or the fluidized bed.

xi) Ultra-low volume liquids (UL)

1-50 wt % of the pesticide are dissolved in up to 100 wt % organic solvent, e.g. aromatic hydrocarbon.

The formulation types i) to xi) may optionally comprise further auxiliaries, such as 0.1-1 wt % bactericides, 5-15 wt % anti-freezing agents, 0.1-1 wt % anti-foaming agents, and 0.1-1 wt % colorants. Preferred composition type is a suspension concentrate.

The agrochemical compositions generally comprise between 0.01 and 95%, preferably between 0.1 and 90%, and most preferably between 0.5 and 75%, by weight of active substance (i.e. pesticide). The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating the pesticide and compositions thereof, respectively, on to plant propagation material, especially seeds include dressing, coating, pelleting, dusting, soaking and in-furrow application methods of the propagation material. Preferably, the pesticide or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The concentration of the alkoxylate of the formula (I) in the ready-to-use preparation (e.g. the tank mix) is in most cases in the range of from 0.01 to 50 g/l, preferably 0.08 to 10 g/l and in particular 0.5 to 8 g/l.

The concentration of water in the ready-to-use preparation (e.g. the tank mix) is in most cases at least 60 wt %, preferably at least 75 wt %, and in particular at least 90 wt %.

The tank mix is usually an aqueous liquid, which is ready to be applied (e.g. by spraying) in the method of controlling phytopathogenic fungi and/or undesired vegetation and/or undesired insect or mite attack and/or for regulating the growth of plants.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising the pesticide and the adjuvant, may be mixed by the user in a spray tank and further auxiliaries and additives may be added, if appropriate. In a further embodiment, either individual components of the composition according to the invention or partially premixed components, e.g. components comprising the pesticide and/or the adjuvant can be applied jointly (e.g. after tank mix) or consecutively.

The present invention furthermore relates to a method of preparing the composition according to the invention by bringing the adjuvant of the formula (I) and the pesticide into contact, e.g. by mixing. The contacting may be done between 5 to 95° C. Thus, a tankmix or a agrochemical composition may be prepared.

The present invention furthermore relates to an alkoxylate of the formula (I)

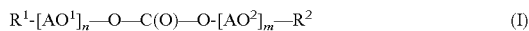

$$R^1\text{-}[AO^1]_n\text{---}O\text{---}C(O)\text{---}O\text{-}[AO^2]_m\text{---}R^2 \qquad (I)$$

where
$R^1$ and $R^2$ are independently a $C_6$-$C_{32}$ hydrocarbon group,
$AO^1$ and $AO^2$ are independently a $C_2$-$C_6$ alkyleneoxy group, and
n and m are independently a value from 2 to 100.

Further forms or preferred forms of $R^1$, $R^2$, $AO^1$, $AO^2$, n, and m are as defined above.

The present invention furthermore relates to a method of controlling phytopathogenic fungi and/or undesired plant growth and/or undesired insect or mite attack and/or for regulating the growth of plants, wherein the composition comprising the pesticide and the alkoxylate of the formula (I) according to the invention are allowed to act on the respective pests, their environment or the crop plants to be protected from the respective pest, on the soil and/or on undesired plants and/or on the crop plants and/or on their environment.

The present invention furthermore relates to a method of controlling phytopathogenic fungi and/or undesired plant growth and/or undesired insect or mite attack and/or for regulating the growth of plants, wherein a composition comprising a pesticide and the adjuvants of the formula (I) according to the invention are allowed to act on the respective pests, their environment or the crop plants to be protected from the respective pest, on the soil and/or on undesired plants and/or on the crop plants and/or on their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or goose-berries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The present invention also relates to seed (such as seeds or other plant propagation materials) comprising the composition according to the invention. Plant propagation materials can be treated preventively with the composition according to the invention at the point of or even before sowing or at the point of or even before transplanting. For the treatment of seed, one will generally use water-soluble concentrates (LS), suspensions (FS), dusts (DS), water-dispersible and water-soluble powders (WS, SS), emulsions (ES), emulsifiable concentrates (EC) and gels (GF). These compositions can be applied to the propagation materials, in particular seed, in undiluted form or, preferably, in diluted form. Here, the composition in question can be diluted 2- to 10-fold, so that from 0.01 to 60% by weight, preferably from 0.1 to 40% by weight, of active substance is present in the compositions used for the seed dressing. The application may be effected before or during sowing. The treatment of plant propagation material, in particular the treatment of seed, is known to the skilled worker and carried out by dusting, coating, pelleting, dipping or soaking the plant propagation material, the treatment preferably being carried out by pelleting, coating and dusting or by in-furrow treatment so that, for example, untimely early germination of the seed is prevented. It is preferred to use suspensions for the treatment of seed. Usually, such compositions comprise from 1 to 800 g/l of active substance, from 1 to 200 g/l of surfactants, from 0 to 200 g/l of antifreeze agents, from 0 to 400 g/l of binders, from 0 to 200 g/l of colorants and solvent, preferably water.

The present invention further relates to a use of the alkoxylate of the formula (I) according to the invention for improving the efficacy of the pesticide. Usually, the efficacy is improved compared to the same use of the pesticide without the alkoxylate of the formula (I).

The advantages of the invention are high stability of the formulation and of the spray mixture, little wind-caused drift in the case of spray applications, good adhesion of the formulation on the surface of the treated plants, increased solubility of the pesticides in the formulation, increased uptake of the pesticides into the plant, or more rapid or enhanced activity of the pesticide (e.g. even at a low dose rate). Other advantages are the high biodegradability of the alkoxylate; the low toxicity of the alkoxylate, the ability of the alkoxylate to lower the surface tension of aqueous compositions, or the increased spreading on plant surfaces; or the low harmful effect against crop plants, i.e. low phytotoxic effects.

The examples which follow illustrate the invention without imposing any limitation.

EXAMPLES

Alcohol Alkoxylate A: ethoxylated (9 EO units) $C_{12}$-$C_{18}$ fatty alcohol.
Alcohol Alkoxylate B: ethoxylated (3 EO units) saturated i-$C_{13}$ alcohol, Brookfield viscosity about 50 mPas (23° C., 60 rpm).
Alcohol Alkoxylate C: ethoxylated (5 EO units) saturated i-$C_{13}$ alcohol, Brookfield viscosity about 85 mPas (23° C., 60 rpm).
Alcohol Alkoxylate D: ethoxylated (7 EO units) saturated i-$C_{13}$ alcohol, Brookfield viscosity about 100 mPas (23° C., 60 rpm).
Alcohol Alkoxylate E: ethoxylated (10 EO units) saturated i-$C_{13}$ alcohol, Brookfield viscosity about 30 mPas (60° C., 60 rpm).
Alcohol Alkoxylate F: ethoxylated (12 EO units) saturated i-$C_{13}$ alcohol, Brookfield viscosity about 40 mPas (60° C., 60 rpm).
Alcohol Alkoxylate G: ethoxylated (3 EO units) $C_{12}$-$C_{18}$ fatty alcohol, pour point <13° C.
Alcohol Alkoxylate H: ethoxylated (5 EO units) $C_{12}$-$C_{18}$ fatty alcohol, solidification temperature about 12° C.
Alcohol Alkoxylate I: ethoxylated (7 EO units) $C_{12}$-$C_{18}$ fatty alcohol, solidification temperature about 15° C.
Alcohol Alkoxylate J: ethoxylated (3 EO units) 2-propylheptanol, HLB about 9.
Alcohol Alkoxylate K: ethoxylated (4 EO units) 2-propylheptanol, HLB about 10.5.
Alcohol Alkoxylate L: ethoxylated (6 EO units) 2-propylheptanol, HLB about 12.5.

Examples 1-15—Preparation of Alkoxylate 199.5 g Alcohol Alkoxylate A (0.33 mol) and diethyl carbonate or dimethyl carbonate (0.23 mol) were mixed with 0.59 g sodium methylate (30% in methanol) and heated to 80° C. while stirring. The temperature was increased to 140° C. and the resulting ethanol was distilled off. When no more ethanol was distilled off, a vacuum of 1 mbar was applied to remove further volatile components. Finally, the composition was cooled to room temperature and filtered. 175 g of the product were obtained as yellowish product. The Alcohol Alkoxylates B to L were reacted with diethyl carbonate accordingly to prepare the alkoxylate of the formula (I) according to the invention (Table 1, column "Educt" depicts Alcohol Alkoxylates A to L.

TABLE 1

Product characteristics (SZ means total acid number; VZ means saponification number; OHZ means hydroxyl number).

| Ex. | Educt | SZ (mg KOH/g) | VZ (mg KOH/g) | OHZ (mg KOH/g) | Water (%) | Density (20° C.; g/cm$^3$) | Refraction ($n_{20}$D) |
|---|---|---|---|---|---|---|---|
| 1 | B | 0.16 | 69 | 29.2 | 0.28 | 0.9552 | 1.4561 |
| 2 | C | 0.12 | 59.2 | 38.6 | 0.13 | 0.9826 | 1.4571 |
| 3 | D | 0.12 | 42.9 | 33.9 | 0.17 | 1.0002 | 1.4601 |
| 4 | G | 0.11 | 70.1 | 32.6 | 0.15 | 0.9512 | 1.4548 |
| 5 | H | 0.11 | 51.1 | 35.8 | 0.15 | 0.9789 | 1.4573 |
| 6 | I | 0.18 | 41.8 | 32.2 | 0.18 | 0.9995 | 1.4595 |
| 7 | J | 0.1 | 99.5 | 8.8 | 0.13 | 0.973 | 1.4512 |
| 8 | K | 0.19 | 81.4 | 12.8 | 0.14 | 0.9829 | 1.4526 |
| 9 | L | 0.18 | 70 | 18.7 | 0.18 | 1.0071 | 1.4565 |
| 10 | I | 0.21 | 49.5 | 18.1 | 0.14 | 1.0037 | 1.4598 |
| 11 | E | 0.19 | 71.9 | 15.8 | 0.14 | 1.0254 | 1.4628 |
| 12 | E | 0.12 | 58.2 | 0.38 | 0.09 | 1.0269 | 1.4611 |
| 13 | A | 0.17 | 41.9 | 13.7 | 0.5 | 1.0168 | 1.4641 |
| 14 | F | 0.13 | 32.8 | 11.7 | 0.14 | 1.0418 | 1.4641 |
| 15 | I | 0.27 | 55 | 1.7 | 0.21 | 1.0079 | 1.46 |

Example 16—Increased Biological Activity

The biological activity was assessed in a greenhouse on wheat (species "Kanzler"), which was infected with *Puccinia triticina* at two leafes stage and incubated for three days at high humidity. The plants were sprayed (spray volume 200 l/ha) with a composition comprising 50 ppm (10 g/ha) epoxiconazole and 100 ppm (20 g/ha) of the respective adjuvant samples from Example 1-15. In the comparative example no adjuvant was added. The plants were further cultivated for ten days at 20-24° C. and 60-90% relative humidity. Finally, the percentage of the infected leaf area (pustules) was visually inspected. Each value was based on three replicates. The results are summarized in Table 2. For comparison, the starting material Alcohol Alkoxylate G was tested, which was used to prepare the product of Example 4.

TABLE 2

| Sample from Example | Infected leaf area |
|---|---|
| —[a)] [b)] | 75 |
| Alcohol Alkoxylate G[a)] | 11 |
| 4 | 8 |

[a)]comparative example.
[b)]without adjvuant

Example 17—Increased Biological Activity

The biological activity was assessed in a greenhouse as described in Example 16 with a reduced dose rate of 2.5 g/ha pesticide. The results are summarized in Table 3. For comparison, the starting material Alcohol Alkoxylate G was tested, which was used to prepare the product of Example 4.

TABLE 3

| Sample from Example | Infected leaf area |
|---|---|
| —[a] | 75 |
| Alcohol Alkoxylate G[a] | 33 |
| 4 | 24 |

[a] comparative example without adjuvant

Example 18—Surface Tension

Physical measurements were done with a solution or dispersion of 1 g/l of the samples from Examples 1-15 in deionized water. The static or equilibrium surface tension is a characteristic value of the interfacial activity of a formulation in the spray solution. Below the critical micelle concentration (CMC) the static surface tension depends on the concentration of the surface active ingredients in the formulation, whereas above the CMC the static surface tension stays constant. The measurement was carried out with the process tensiometer Kruess K 100 using the Wilhelmy-Plate-Method. During the measurement the bottom line of a vertical hanging platinum plate is wetted by the liquid to be analyzed. The force with which the plate is pulled into the liquid is measured and can be converted into the surface tension of the liquid in mN/m. 40 mL of the prepared spray solution are filled into Teflon troughs in the apparatus and the surface tension is detected. The static surface tension is calculated once five successive measuring points match within 0.1 mN/m. The results are summarized in Table 4.

TABLE 4

| Sample from Example | Based on Alcohol Alkoxylate | Surface Tension [mN/m] |
|---|---|---|
| 6 | I | 30 |
| 5 | H | 33 |
| 4 | G | 29 |
| 9 | L | 29 |
| 8 | K | 28 |
| 7 | J | 28 |
| 3 | D | 30 |
| 2 | C | 29 |
| 1 | B | 28 |

Example 19—Increased Uptake Rate

Wheat plants (*Triticum aestivum* variety Me/on) were cultivated in the greenhouse for 6 weeks up to development stage BBCH 39. The plants were transferred to an automatic lab track sprayer and they were sprayed with 125 g/ha epoxiconazole, 125 g/ha fluxapyroxad, and 250 g/ha of the respective adjuvant according to the following parameters:
Water amount: 200 l/ha
Nozzle type: Air injector, ID 120 02 (Lechler, Germany)
Speed: 1.4 m/s
Pressure: 3.33 bar Subsequently to spraying, the plants were cultivated again in the greenhouse under ambient conditions. After 8 days samples of 10-15 treated leaves were cut off and weighed.

Leaves were cut into small pieces, transferred into glass bottles and washed with 50% methanol in demineralized water as washing medium for 5 min. Then, the washing medium was separated from the leaves. The leaves were washed again with washing medium for 5 min. Both washing media were combined and diluted for analysis.

Finally, the leaves were transferred to a vial containing the extraction medium (75% methanol, 20% water and 5% HCl) and homogenized using a Polytron PT 6100 dispersing unit (Kinematica, CH) for 2 min. 10 ml of the extract were centrifuged with 4000 rpm for 5 min. 2 ml of the supernatant were treated with 2 ml NaOH (0.2 mol/L) and 5 ml cyclohexane, and stirred for 30 min and centrifuged subsequently. 1 ml of the cyclohexane phase was transferred to a glass vial and dried (Liebisch $N_2$ Evaporator, Germany). The residue was solubilized in methanol/water 50:50 and analyzed by HPLC-MS/MS.

An Agilent 1100 series HPLC coupled to an Applied Biosystems API 3000 triple quadrupole mass spectrometer, equipped with an electro spray ionization source, was used. The mass spectrometer was operated in the MS/MS positive ion mode with multiple reaction monitoring (MRM) using two transitions per analyte at optimized conditions. In addition, unsprayed plants were treated in the same way to see whether they are contaminated. Unsprayed leaves were spiked with standard active ingredient to determine the recovery of active ingredient during washing and extracting steps. According to the recovery rate the measured sample values were corrected. The results were summarized in Table 5.

For comparison, the starting material Alcohol Alkoxylate G was tested, which was used to prepare the product of Example 4. For another comparison, the starting material Alcohol Alkoxylate H was tested, which was used to prepare the product of Example 5.

The data showed that the uptake rate of epoxiconazol and fluxapyroxad were increased when using the adjuvants according to the invention.

TABLE 5

| | Uptake rate | |
|---|---|---|
| Sample of Example | Epoxiconazole Uptake Rate [%] | Fluxapyroxad Uptake Rate [%] |
| —[a],[b] | 8 | 4 |
| Alcohol Alkoxylate G[a] | 36 | 23 |
| 4 | 62 | 38 |
| Alcohol Alkoxylate H[a] | 35 | 21 |
| 5 | 56 | 39 |

[a] comparative example.
[b] without any adjuvant

Example 20—Increased Biological Activity

The biological activity was assessed in a greenhouse on wheat (species "Kanzler"), which was infected with *Puccinia triticina* at two leafes stage and incubated for three days at high humidity. The plants were sprayed (spray volume 200 l/ha) with a composition comprising 50 ppm (10 g/ha) epoxiconazole and 100 ppm (20 g/ha) of the respective adjuvant samples (column "10 g/ha dose rate"). As alternative the dose rate of 50 g/ha epoxiconazole and 100 g/ha adjuvant were tested (column "50 g/ha dose rate"). In the comparative example no adjuvant was added. The plants were further cultivated for ten days at 20-24° C. and 60-90% relative humidity. Finally, the percentage of the infected leaf area (pustules) was visually inspected. Each value was based on three replicates. The results are summarized in Table 6.

TABLE 6

| Sample from Example | Infected leaf area 50 g/ha dose rate | Infected leaf area 10 g/ha dose rate |
|---|---|---|
| —[a] | 75 | 75 |
| 15 | 6 | 6 |
| 5 | 6 | 6 |
| 4 | 7 | 7 |
| 3 | 18 | 18 |

[a] comparative example without adjuvant

We claim:

1. An alkoxylate of the formula (I)

$$R^1\text{-}[AO^1]_n\text{—}O\text{—}C(O)\text{—}O\text{-}[AO^2]_m\text{—}R^2 \quad (I)$$

wherein:
- $R^1$ and $R^2$ are independently 2-propylheptyl,
- $AO^1$ and $AO^2$ are independently a $C_2$-$C_6$ alkyleneoxy group, and
- n and m are independently a value from 2 to 100.

2. The alkoxylate of claim 1, wherein $AO^1$ and $AO^2$ are independently selected from ethyleneoxy, propyleneoxy, butyleneoxy, and mixtures thereof.

3. The alkoxylate of claim 1, wherein $AO^1$ and $AO^2$ are independently selected from ethyleneoxy, propyleneoxy, and mixtures thereof.

4. The alkoxylate of claim 1, wherein $AO^1$ and $AO^2$ are independently ethyleneoxy, or a mixture of ethyleneoxy and propyleneoxy.

5. The alkoxylate of claim 1, wherein n and m are independently a value from 2 to 50.

6. The alkoxylate of claim 1, wherein n and m are independently a value from 2 to 20.

7. The alkoxylate of claim 1, wherein n and m are independently a value from 3 to 13.

8. The alkoxylate of claim 1, wherein the ratio of n to m is from 10/1 to 1/10.

9. The alkoxylate of claim 1, wherein the ratio of n to m is from 3/1 to 1/3.

10. The alkoxylate of claim 1, wherein the ratio of n to m is from 1.5/1 to 1/1.5.

11. The alkoxylate of claim 1, wherein:
- $AO^1$ and $AO^2$ are independently selected from ethyleneoxy, propyleneoxy, butyleneoxy, and mixtures thereof;
- n and m are independently a value from 2 to 50; and
- the ratio of n to m is from 10/1 to 1/10.

12. The alkoxylate of claim 1, wherein:
- $AO^1$ and $AO^2$ are independently selected from ethyleneoxy, propyleneoxy, and mixtures thereof;
- n and m are independently a value from 2 to 20; and
- the ratio of n to m is from 3/1 to 1/3.

13. The alkoxylate of claim 1, wherein:
- $AO^1$ and $AO^2$ are independently ethyleneoxy, or a mixture of ethyleneoxy and propyleneoxy;
- n and m are independently a value from 3 to 13; and
- the ratio of n to m is from 1.5/1 to 1/1.5.

14. The alkoxylate of claim 1, wherein:
- $AO^1$ and $AO^2$ are independently ethyleneoxy;
- n and m are independently a value from 3 to 13; and
- the ratio of n to m is from 1.5/1 to 1/1.5.

* * * * *